United States Patent [19]

Biagi

[11] 4,167,187

[45] Sep. 11, 1979

[54] DUAL EPILATION MACHINE

[75] Inventor: Alvaro D. Biagi, Huntington Station, N.Y.

[73] Assignee: Kree Institute of Electrolysis, Inc., New York, N.Y.

[21] Appl. No.: 778,361

[22] Filed: Mar. 17, 1977

[51] Int. Cl.² ............................................. A61N 3/04
[52] U.S. Cl. ............................ 128/303.13; 128/303.18
[58] Field of Search ...................... 128/303.13, 303.14, 128/303.17, 303.18

[56] References Cited

U.S. PATENT DOCUMENTS

| 2,700,975 | 2/1955 | Hopfinger et al. | 128/303.18 |
| 2,888,927 | 6/1959 | Fozard | 128/303.13 |
| 3,315,678 | 4/1967 | Donelson | 128/303.18 |
| 3,359,982 | 12/1967 | Guiorguiev | 128/303.18 |
| 4,051,855 | 10/1977 | Schneidenman | 128/303.14 |

FOREIGN PATENT DOCUMENTS 2044078  5/1972  Fed. Rep. of Germany ...... 128/303.14

Primary Examiner—Lee S. Cohen
Attorney, Agent, or Firm—Gottlieb, Rackman & Reisman

[57] ABSTRACT

A dual epilator for removal of unwanted hair. Line power is reduced and rectified in a power supply which energizes a timer circuit and an RF amplifier. A timed DC pulse emitted from the timer circuit under an operator's regulation feeds a normally unenergized crystal controlled oscillator whose output is boosted in the RF amplifier. The RF power can be selectively utilized by a needle or tweezers. A tuned antenna provides an efficient return for the RF power.

22 Claims, 8 Drawing Figures

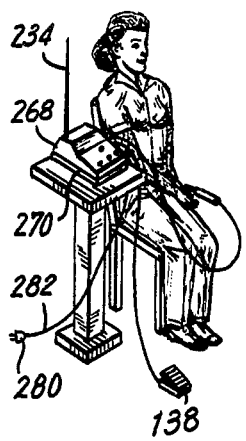
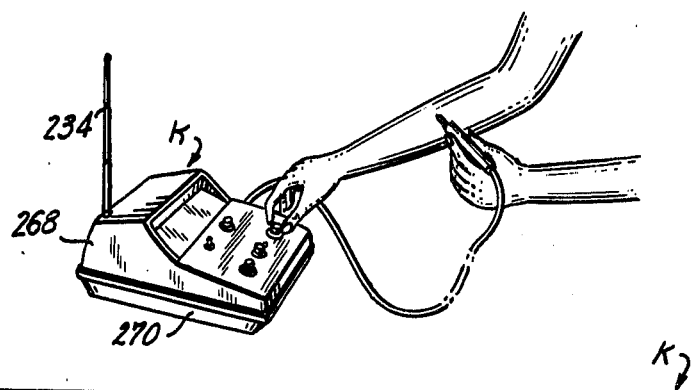
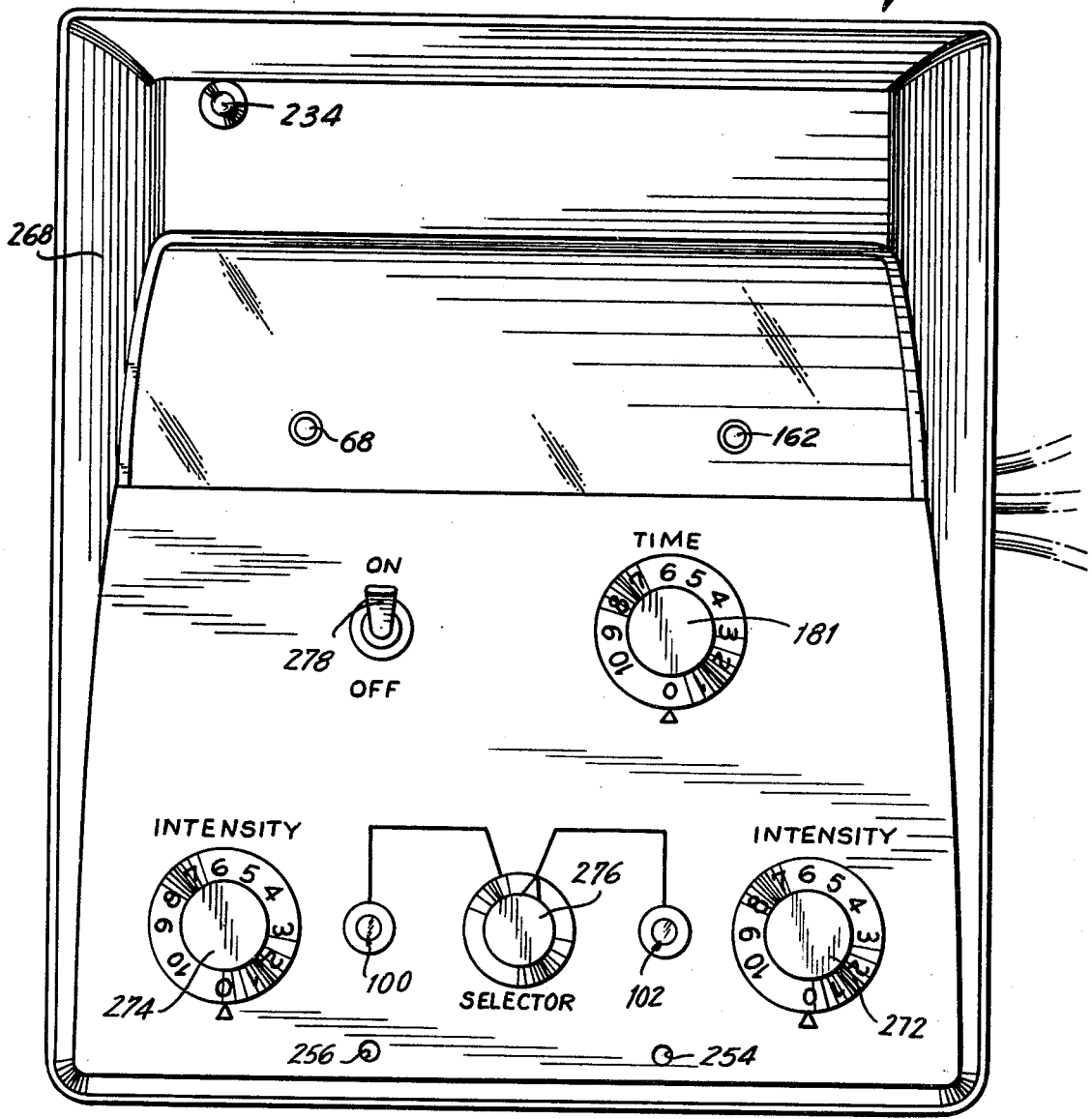
FIG. 7
FIG. 8
FIG. 6

DUAL EPILATION MACHINE

BACKGROUND OF THE INVENTION

1. Field of the Invention

Process and equipment for electrical depilation.

2. Description of the Prior Art

The removal of hair has been of human concern for ages. Methods like plucking, sanding, waxing, shaving, chemical deterioration and galvanic action are subject to various limitations. The most serious disadvantages of some of these methods are that they may lead to infections, rashes and skin irritations. To avoid some of these problems, short wave electrical machines have been devised.

A hair strand can be removed by using a tweezer which grips the strand. Radio frequency power is applied through the tweezer to the strand for the purpose of hair removal. Another way is to insert a needle into a hair follicle and to supply RF power to the needle and from the needle to the growth cells area of the follicle.

A single method is not suitable for all applications for hair removal since hair growth can be quite different depending upon its location on the body, the type of hair involved, and the type of follicles and growth cells area, as well as pain and irritation on different locations on the body.

In the use of radio frequency hair removal, the human body forms part of the circuit. This requires completely safe machines and procedures.

Many of the older radio frequency generators do not employ a narrow frequency band. Rather, their output ranges over a wide band of frequencies. Many of these frequencies interfere with frequencies assigned for communication purposes. Furthermore, the Federal Communications Commission has developed standards for the emission of radio frequencies which are not met by a number of older machines.

In addition, highly skilled operators or at least a second person were needed to perform the removal of hair when using some of the older machines.

Another disadvantage of conventional RF systems is the imposition of RF energy on the house power line.

SUMMARY OF THE INVENTION

1. Purposes of the Invention

It is an object of the invention to provide a versatile epilator for the removal of hair.

It is another object of the invention to provide an epilator system that is very effective in the use of radio frequency power.

It is another object of the invention to provide an epilator system which minimizes the necessary radio frequency power conducted through the human body for epilation.

It is another object of the invention to provide an epilator system which allows the use of more than one hair removal method embodied in the machine—e.g., by needle or tweezer.

It is another object of the invention to provide an epilator which allows precise timing of the period of radio frequency exposure of the hair to be removed.

It is another object of the invention to provide an epilator which reduces the broadcast of RF radiation in order to avoid interference with other electronic equipment.

It is another object of the invention to provide an epilator which minimizes the interference with radio frequency communication channels by avoiding the broadcasting of broad bands of radio frequency.

It is another object of the invention to provide an epilator which is reliable and easy to service.

It is another object of the invention to provide an epilator which minimizes the radio frequency power picked up by the house power line.

It is another object of the invention to provide an epilator which is highly efficient as fabricated and whose efficiency is independent of the RF impedance of the location and its house power line.

It is another object of the invention to provide an epilator with a balanced dipole construction where essentially the same voltage occurs at the antenna tip and at the probe tip.

Other objects of the invention, in part, will be obvious and, in part, will be pointed out hereinafter.

2. Brief Description of the Invention

According to the present invention, the foregoing, as well as other objects, are achieved by constructing an epilator that includes an antenna, a crystal-controlled RF oscillator, an integrated circuit timer and a dual mode needle/tweezer output. A power supply adapted to be connected to an AC line supplies DC energy. DC power is fed through an operator-controlled momentary switch to an operator-settable variable timer for starting a timed DC pulse. The pulse energizes the RF oscillator and its output is boosted by the RF amplifier. The output of this amplifier is connected via an operator-controlled selector dwell switch and power-limiting resistors to either a needle or a tweezer.

Inserting the needle into the hair follicle, the operator closes the momentary switch, whereupon a radio frequency pulse is applied directly to the growth cells area of the hair for the purpose of coagulating said cells. Applying power to the tweezer is for the purpose of hair removal. An antenna connected to the amplifier return reduces the resistance of the RF return path and reduces broadcast of radiation.

This system is very effective in using and applying radio frequency power to hair removal. It allows a selection of either a needle or a tweezer for efficient use of power and for patron requirements.

The needle operation time of the RF energy is precisely controlled by the timer so that unnecessary transformation of radio frequency power into heat due to longer exposures than sufficient to coagulate the growth cells area of the hair is easily controlled. The employment of an impedance matched antenna for shunting the RF circuit through the body improves the concentration of the radio frequency power applied to the person.

The present invention provides a very versatile method of epilation. Not only is it possible to set time and intensity of power applied, but a choice between different hair-contacting devices is provided. Each method individually provides for a wide range of application in the art of hair removal, as does the feature of dual epilation in one machine.

The RF power pulse is generated almost instantly upon closure of the control switch, thus resulting in efficient operation. For the effective coagulation of the growth cells area in needle operation, a threshold of heat generation has to be reached and sustained for a very short, preselected, measured period of time.

A particular advantage in this context is the employment of the tuned antenna. Conventional epilators rely upon the environment and power lines for a return, these being uncontrollably variable and therefore inconsistent and inefficient. The antenna of the present invention provides a controlled low impedance return path for the radio frequency power and collects the same from the body. The employment of the antenna simultaneously enhances safety and efficiency in hair removal with radio frequency.

The present invention provides an RF dipole for most efficient operation. The casing around the RF generator provides the current lobe and the voltage node of the dipole, and the probe end and the antenna end present the points of highest voltage of the dipole. This balance of the dipole and the suppression of higher order oscillator modes result in high voltage at the removal point and little waste or unused radiation of RF frequency.

An additional result of the balancing is that minimal RF voltage is present between the metal casting of the RF generator and ground.

Another feature of the present invention is the reduction of RF interference with other electronic equipment. Many modern electric and magnetic devices are sensitive to perturbation by radio frequency energy. Especially annoying is the interference of radio frequency energy with communication channels, radio and television. The present invention minimizes possible interference in several respects. As pointed out above, the total amount of radio frequency energy applied is reduced by the provision of timed pulses, a short rise time of the pulse and by the impedance reduction by utilization of an antenna. While the total power employed is reduced by the antenna, there is the additional effect that the amount of RF energy emitted into the environment is reduced by the antenna reception and return of emitted radio frequency waves. Interference with communication frequencies is further minimized by employment of a crystal-controlled oscillator with a narrow frequency band as a source and thus the generation of broad band radio frequency energy is extremely small. These features of the present invention result in a minimum of interference with communication devices.

The incorporation of advanced components like an integrated circuit and a crystal-controlled oscillator in the present invention results in a reliable and easily serviceable unit. As pointed out in more detail in the description of the preferred embodiment, it is very advantageous from a servicing point of view to have all switching and indicating devices mounted on an upper cover and the functional devices on a base. A sevenfold connector and a separate RF connector provide for electrical contacts. This allows for easy diagnosis and accessibility of any circuit defects which might occur.

The invention consists in the features of construction, combination of elements, arrangement of parts and series of steps which will be exemplified in the device and method hereinafter described and of which the scope of application will be indicated in the appended claims.

BRIEF DESCRIPTION OF THE DRAWINGS

In the accompanying drawings in which are shown various possible embodiments of the invention:

FIG. 6 is a top view of the dual epilator control board;

FIG. 7 is a perspective view of the dual epilator in position for operation; and FIG. 8 is a perspective view of the dual epilator in use.

DESCRIPTION OF THE PREFERRED EMBODIMENTS

Figure 1:
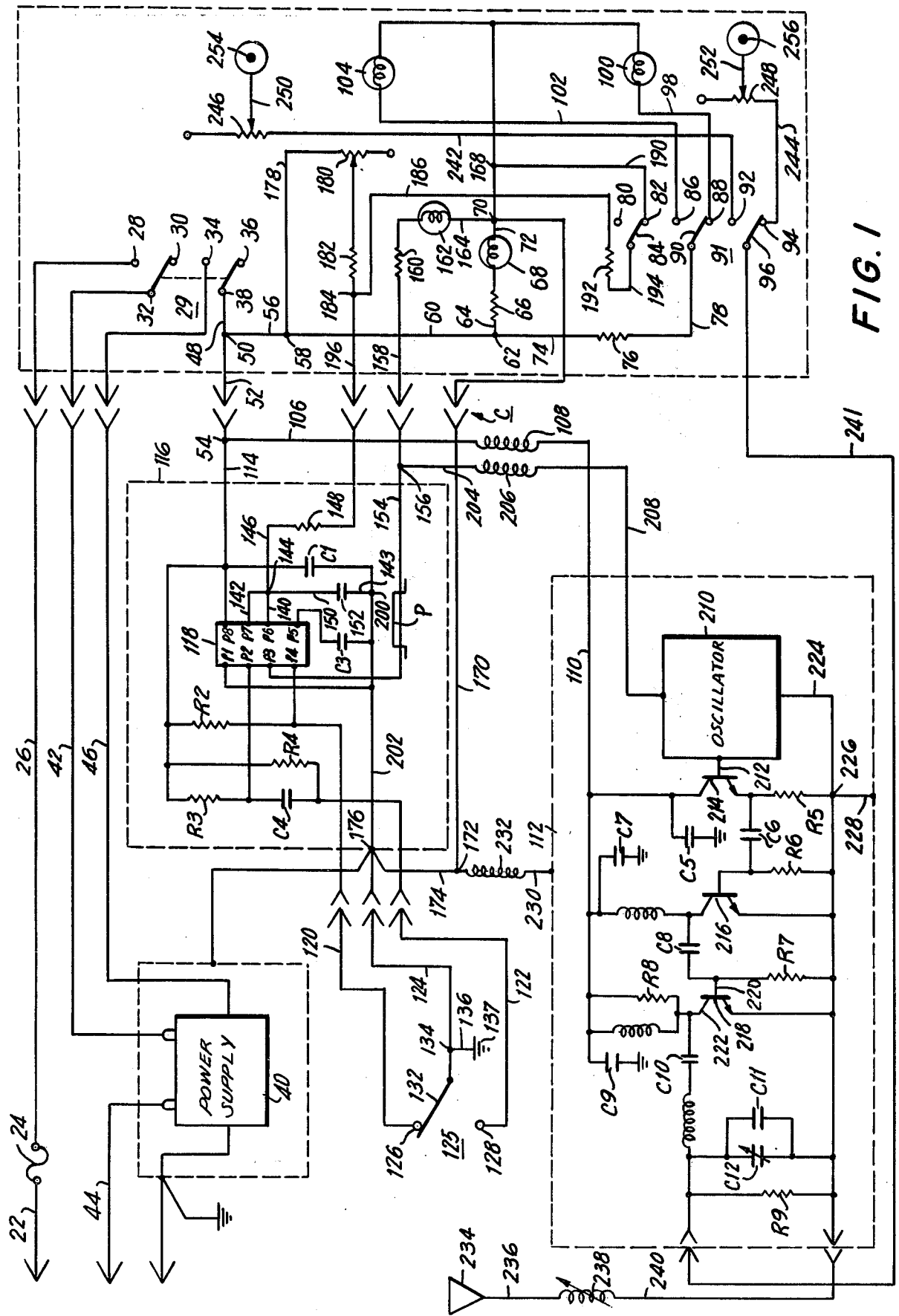
FIG. 1 is a schematic circuit diagram of a first dual epilator embodying the present invention.

Referring now in detail to FIG. 1, a hot lead 22 of an incoming alternating current 110 volt source is fed to a fuse 24; a fuse capable of carrying 1 amp. of current is suitable. From the fuse 24, a hot lead 26 runs to a contact 28 of a manually operable on-off double-pole double-throw power switch 29 including contacts 28, 30, 34, 36, and ganged blades 32 and 38. The switch is arranged to simultaneously connect the power input contact 28 and the power output contact 34 of a DC power supply 40 in circuit. The contacts 30 and 36 are dead, the switch 29 shown in FIG. 1 being in "off" condition. A lead 42 provides the hot AC input from the blade 32 to a DC power supply 40 and a lead 44 provides the connection to the neutral of said power line. The power supply 40 employed is an LOS-Z-12 Lambda commercial regulated unit. Its rated input range is 105–125 VAC and its rated frequency range is 47 to 63 Hz. Its maximum output rating is 12±5% VDC and 1.6 amps. at 40° C.

The DC output of the power supply 40 connects via a lead 46 to the contact 34 of the switch 29. With the power switch closed, the DC power leaving the blade 38 through a wire 48 branches at a junction point 50 via a lead 52 to a junction point 54 (through one detachable coupling of a sevenfold connector C the couplings of which are shown in FIG. 1 but will not be described) and via a lead 56 from the junction point 50 to a junction point 58. From the junction point 58 a lead 60 runs to a junction point 62 and from the junction point 62 a wire 64 carries DC current through a current-limiting resistor 66 to a "power on" indicator lamp 68 which is connected to a junction point 70 via a line 72. Another lead 74 from the junction point 62 runs to a current-limiting resistor 76, a wire 78 connecting said resistor 76 to a blade 90 of a triple-pole double-throw selector switch 91 having contacts 80, 82, 86, 88, 92, 94, and ganged blades 84, 90, and 96. In down (tweezer) position the switch 91 selectively connects the wire 78 to the contact 88 and via a lead 98 to a left (tweezer) indicator lamp 100. In up position the switch 91 connects the wire 78 to the contact 86 and via a lead 102 to a right (needle) indicator lamp 104. Lamps 100 and 104 are preferably light-emitting diodes of different colors.

From the junction point 54 DC power runs through a wire 106, an isolating coil 108 and a wire 110 to an RF amplifier 112 which thus is energized as long as the power switch 29 is in "on" position. Another DC power line 114 runs from the junction point 54 to a timer assembly 116.

The core of the timer assembly 116 typically is an eight-pin NE555V integrated circuit 118, with pins P1, P2, P3, P4, P5, P6, P7, and P8, manufactured by Signetics Corporation. The timer circuit is connected for operation via leads 120, 122, 124 to a single-pole double-throw operator-controlled momentary switch 125 having contacts 126, 128 and a blade 132. The wire 124 has a junction point 134 which connects to a ground 137 via a lead 136. When the blade 132 of the switch 125 engages the contact 128, a timing cycle is started and when blade 132 engages the contact 126, the timer 116 is reset in case of needle operation and turned off when the tweezer mode is used. A foot pedal 138 controls the switch 125, thus allowing an operator to use both hands for manipulating the needle/tweezer. The blade of the switch is biased to engage the contact 126.

Several resistors and capacitors associated with the timer assembly 116 and external to the integrated circuit serve to adapt the integrated circuit 118 to the requirements of the present invention.

Contained within the integrated circuit 118, as is well known, are two comparators, one flip-flop resettable circuit, an output DC amplifier, and a discharge transistor. The pins P6 and P7 of the integrated circuit 118 are connected via leads 140 and 142 to a junction point 144 which is connected to an external RC time constant circuit provided by a resistor 148, in part, and a capacitor 152 connected in series between the DC power line 56 and ground by circuit including the leads 146 and 150. The pin P6 is one input to one of the two comparators having a precise voltage as a second input. When the voltage on the pin P6 is equal to the DC voltage on the second input to the comparator, the resettable flip-flop circuit toggles and the discharge transistor connected to the pin P7 is turned on, discharging the time constant circuit voltage.

Normally, the flip-flop is inactive because is reset pin P4 is grounded by the external switch 125. However, when the pin P4 is ungrounded and the pin P2 has a trigger pulse applied to the second comparator, upon actuation of the switch 125, the flip-flop is held at the state where the output at the pin P3 is near the DC supply level and the transistor controlling pin P7 is at cutoff. When the voltage on the pins P6 and P7 reaches the critical value required by the comparator at the pin P6, the flip-flop is activated to discharge the voltage at the pins P6 and P7, provided that the reset terminal pin P4 is not grounded.

Before operation begins, the switch 125 is in its idle reset position with the blade 132 engaging the contact 126. This provides a connection to the ground 137 for the pin P4. At the same time the discharge pin P7 and the threshold pin P6 are at near ground potential. A trigger is absent at the trigger pin P2 and there is a zero output from the output pin P3. Upon actuation of the switch 125 to "on" position by engaging the blade 132 with the contact 128, a momentary trigger pulse is applied to the terminal of the trigger pin P2 and at the same time the reset pin P4 is ungrounded and remains ungrounded as long as the blade 132 is disengaged from the reset contact 126. Thereupon the full voltage of an output pulse appears at the output pin P3 from which it is applied to a crystal-controlled oscillator 210 via a line 154 through a junction point 156, another line 204, an RF isolating coil 206 and a line 208. From the start of the pulse on the pin P3 an exponential rise of the voltage on the pins P6 and P7 occurs, and its time constant is determined by the external RC time constant circuit aforementioned. When the voltage on the pins P6 and P7 equals the value which will trigger and flip-flop at which time the pulse on pin P3 ends, the voltage at pins P6 and P7 will be grounded and will remain so until engagement of the blade 132 with the contact 126 resets the voltage at the pin P4 by grounding it. If at any time during the pulse the reset pin P4 is grounded, the output voltage at the pin P3 will be terminated before the time constant voltage at this junction point 144 reaches the value which will cause automatic termination.

In case of needle operation, the switch 91 is in up position so that the blade 84 engages the dead contact 80 and the voltage at the pins P6 and P7 therefore can rise to the trigger level of the flip-flop.

When tweezer operation is desired, the switch 91 is moved to down position in which the blade engages contact 82 and provides a path from the pins P6 and P7 to the ground 137 via the junction points 144 and 184, a lead 186, a resistor 192, the blade 84, the contact 82 and the junction points 168, 70, 176, and 134. This prevents the voltage on the pins P6 and P7 from reaching the level necessary to trigger the flip-flop. Therefore, in the tweezer operation the timing pulse will run indefinitely as long as the blade 132 engages the contact 128, and the pulse only will terminate when the blade 128 engages the reset contact 126. This arrangement automatically limits the duration of RF power output in the needle mode, but is operator-controlled for the tweezer mode.

Upon starting the timer cycle by grounding the wire 122, the timer assembly 116 provides a timed DC output pulse which runs through a wire 154 to a junction point 156. From the junction point 156 a wire 158 leads the pulse through a resistor 160 and to a pulse indicator lamp 162 which emits visible light as long as the pulse persists. The lamp 162 is connected with a wire 164 to the junction point 70.

The junction point 70 is connected to the ground 137 by a wire 170, the junction point 172, a lead 174, the junction point 176, the lead 124, the junction point 134 and the lead 136.

DC power is branched off at the junction point 58 via a lead 178 to a timer control 180 which is a variable resistor regulated by a knob 181 (see FIG. 6) and which determines the duration of the pulse P. The pulse length for needle operation can be varied between about 1/20 of a second and about two seconds. In tweezer operation the timer control resistor 180 has no effect, the time being determined by the engagement time of the blade 132 with the contact 128 of the switch 125.

The DC output of the power supply 40 is fed from the junction 58 through the variable resistor 180 and a current limiting resistor 182 to the junction point 184. From the junction point 184 one wire 186 is connected to a resistor 192 which with a wire 194 is connected to a blade 84 of the triple-pole selector switch 91 for selectively providing a shunt to the ground 137. When the tweezer mode is operative via a wire 190 to the junction points 168, 70, 172, 176 and 134 by voltage divider action, a definite voltage is established at the junction point 184 and its connection through the wire 196, the resistor 148 and the wire 146 to the junction point 144 and from there to the pins P6 and P7 limits the voltage on these pins. When the needle mode is in operation the shunting circuit is interrupted between blade 84 and the contact 82; hence, the voltage at the junction point 184 can rise to the full DC voltage and correspondingly the voltage on the pins P6 and P7 can cross the level required for switching the flip-flop. This ensures the provision of a short pulse when a needle is inserted into a follicle for coagulation of the growth cells area. On the other hand, when using a tweezer for gripping a hair, the circuit of the present invention provides continuous radio frequency power in the tweezer mode as long as the blade 132 engages the contact 128.

The DC output pulse from the pin P3 to fed through an RF isolating coil 206 and a wire 208 to the crystal-controlled oscillator 210 which, as well known, has a narrow output band. The oscillator 210 typically is a model 231-2709 sold by Vectron Laboratories, Inc. of Norwalk, Connecticut, having a frequency of 27.12 MHz. The output of the oscillator 210 (about 100 milli-amps) is fed through a wire 212 and is boosted by the RF amplifier 112. Since the amplifier 112 is always engaged as long as the power switch 29 is "on", amplification occurs immediately so that the resulting pulse of RF power output has a fast rise time.

The RF amplifier 112 is of the class C type and comprises three transistorized stages using transistors 214, 216, and 218. Transistor 214 is a 2N5172, 216 is a 2N5589 and 218 is an A25-12. The transistor 214 is driven by the output from the crystal-controlled oscillator 210 supplied by the lead 212. The transistor 214 is biased to optimize a large negative going pulse in its collector. The negative going pulse repeats at the same rate as the crystal oscillator drive. Bias of the transistor 218 is set at near full conduction and requires a large negative swing on the transistor base 220 to turn the transistor off. The turnoff of the transistor 218 generates a large positive going inductive pulse on the collector 222. The output circuit is tuned to the frequency of the positive going pulses. The resonance of the output circuit causes the current flowing in the load to be completely sinusoidal with harmonic outputs at least 30 db below the fundamental. The ground connection for the crystal-controlled oscillator 210 runs through a wire 224, a junction point 226 and a lead 228 to the RF amplifier metal mounting chassis which is connected to the house ground 137 via a lead 230 and an inductive isolating coil 232 and then by the wire 174 to the junction point 176.

Both the RF oscillator 210 and RF amplifier 112 are mounted on the chassis which acts as a heat sink and also shields and prevents the broadcast of the radio frequency radiation.

To provide a low impedance circuit for the RF power used in removing hair and to avoid emitting unnecessary radiation into the environment via power lines, a tuned antenna 234 is connected through a wire 236 to a tunable loading coil 238 and via a wire 240 to a junction point 226 and then, as described above, to the ground 137 via the isolating coil 232. The antenna and loading coil are tuned to obtain maximum power transfer. A telescoping antenna is preferred.

The output of the RF amplifier is connected via a lead 241 to a blade 96 of the three-pole double-throw mode selector switch 91. From there, depending on the state of said switch, it is selectively connected from a contact 92 or 94 via a wire 242 or 244 to either of two intensity-limiting variable resistors 246 or 248 and through a wire 250 or 252 to two output jacks 254 or 256. One of the jacks is shaped to receive a plug 258 connected to a needle 260. The other jack 256 is shaped to receive a plug 262 connected to a tweezer 264. The three-pole switch 91 coordinates the illumination of the indicator lamp 104 or 100 for each mode, the nature of the time span of the output pulse, and the energization of the desired jack 254 or 256.

Figure 2:
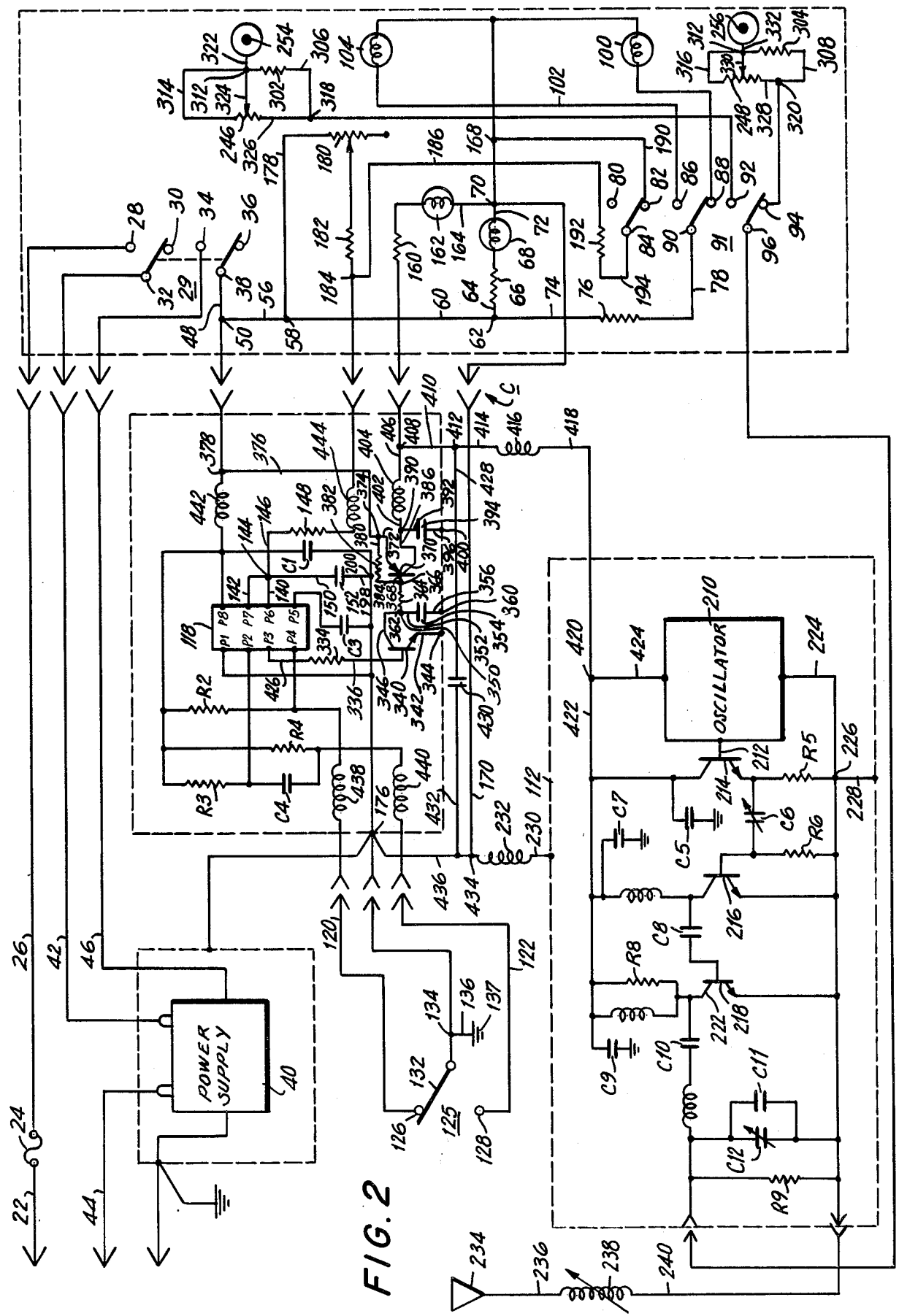
FIG. 2 is a schematic circuit diagram of a second dual epilator embodying the present invention.

An alternate electric circuit for the epilation is shown in FIG. 2 wherein all identical parts are identically numbered. This circuit avoids the possibility of inducing regenerative energization of the oscillator by concurrently energizing the oscillator and the RF amplifier only when RF power is required. It also provides certain optional modifications. The use of the resistors 248 and 246 is supplemented by additional resistors in parallel. This is done by introducing two additional resistors 302 and 304. A wire 306 connects the resistor 302 between a junction point on the wire 242 and a junction point 312 on the wire 322 to the jack of the needle mode. In parallel a wire 326 runs from the junction point 318 to the resistor 246 serving as a potentiometer. A wire 314 runs from the other terminal of the potentiometer to the junction point 312. This serves as a continuous circuit for the power to the needle mode. In order to change the power to the needle the potentiometer 246 is variable and by varying the position of its tap and connecting its tap by a wire 324 to the junction point 312 it is possible to vary the radio frequency power which is available to the needle. This is done in an analogous fashion for the tweezer. The junction point 320 on the wire 244 has one branch connected through a wire 308 to the resistor 304 and then to a junction point 312 and from there through wire 332 to the jack of the tweezer. In parallel to this connection a wire 328 runs from the junction point 320 to the potentiometer 248. A wire 316 runs from the potentiometer 248 to the junction point 312. Thus there is always a certain power level available for the tweezer as soon as the timer circuit is initiated. In order to vary the power available to the tweezer, the position of the tap on the potentiometer 248 is changed.

Another modification consists in a second mode for providing power to both the RF oscillator and the RF amplifier when the timer is actuated to emit a DC pulse. Instead of feeding power continuously to the RF amplifier and pulsing the oscillator, the circuit amplifies the timer signal and rapidly supplies sufficient power to both the RF oscillator and the RF amplifier to energize the same almost instantaneously and simultaneously. The output of the timer circuit 116 is fed through a wire 426, a resistor 334 and a wire 336 to the base of a transistor 340. This transistor 340 is a low power driver transistor for which a general purpose NPN transistor can be used such as a 2N2222. The emitter of the transistor 340 is connected to ground by a wire 342 through a junction point 344. The output of the transistor 340 is fed from its collector through a wire 346 to a junction point 350 which is connected by a wire 352, a capacitor 354 and a wire 356 to a junction point 360 at ground. From the junction point 350 the amplified output of the transistor 340 is fed through a wire 362 and a resistor 364 to a junction point 366 which is connected through a wire 368 to the base of a transistor 370. The transistor 370 typically is an MJE 105 power transistor that provides fast and sufficient power to both the RF oscillator and the RF amplifier. DC supply power is taken off at a junction point 378 and fed through a wire 376 to junction point 374 and from there through a wire 372 to the emitter of the transistor 370. In addition, a connection is provided from the junction point 374 through a wire 380, resistor 382 and a wire 384 to the junction point 366. This resistor 382 is a current-limiting resistor for the base of the power transistor 370. The output of transistor 370 from its collector is fed through a wire 386 to a junction point 390 that is connected to ground at a junction point 400 by a wire 392 through a capacitor 394 and wire 396. The principal purpose of the capacitors 354 and 394 is filtering. The DC power pulse output from the junction point 390 is fed through a wire 402, an induction coil 404 and a wire 406 to a junction point 408 and from said junction 408 through a wire 410 to a junction point 412. The junction point 412 is connected by a wire 414 to a second filtering induction coil 416 and thence through a wire 418 and to a junction point 420 where it branches off through a wire 424 to feed the RF oscillator and through a wire 422 to feed the RF amplifier. Another connection for filtering purposes is made from the junction point 412 through a wire 428, a capacitor 430 and a wire 432 to a junction point 434 which is connected through a wire 436 to ground 176.

Improved radio frequency isolation of the timer assembly is obtained by introducing additional induction coils 438, 440, 442 and 444 as shown in FIG. 2.

Some of the circuitry can be simplified by elimination of some components. For instance, as shown in FIG. 2 the resistor R7 of FIG. 1 has been eliminated from the RF amplifier without a marked change in the performance of the circuit.

Figure 3:
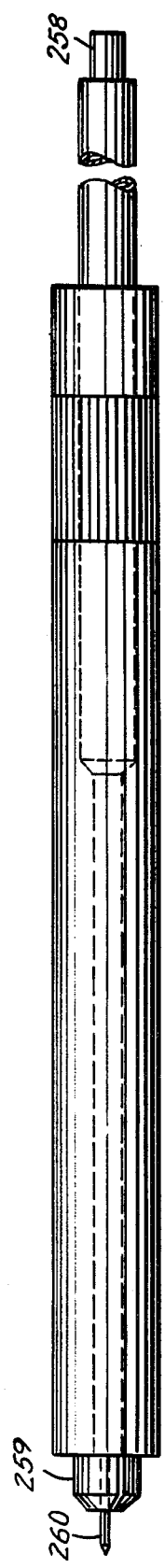
FIG. 3 is a schematic diagram of an epilator needle and holder.
Figure 4:
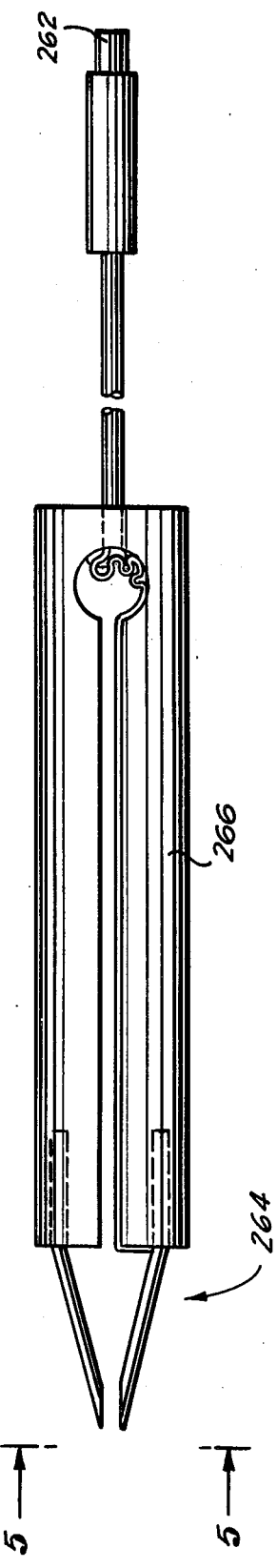
FIG. 4 is a schematic diagram of a tweezer probe assembly.
Figure 5:
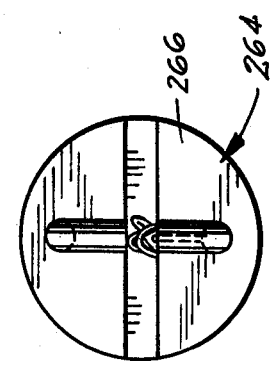
FIG. 5 is a front view of the tweezer probe, as viewed from the line 5—5 of FIG. 4.

A needle collet 259 (FIG. 3) releasably holds the needle 260 through a chuck and can be made, e.g., from brass or soft stainless steel. The needle 260 projects about ¼" from the holder and preferably is about 5 mils(⅛ mm) in diameter.

A holder 266 for the tweezer tips is about 5" long and 1" thick. It may be made from a synthetic plastic, e.g. a polycarbonate. The tweezer tips 264 may be made from stainless steel rod.

A dual epilator is run from a console K that includes a cover 268 which supports indicator lamps, switches, and controls and is removable from a base 270 that supports the power supply 40, the timer assembly 116, the RF generator 210,112, and the antenna 234. The variable resistors 246, 248 that control the intensity of RF power supplied to the needle and tweezer are operable by manipulation of knobs 272, 274 on the cover. The knob 181 on the cover controls the duration of the RF power pulse when the switch 91 is on the needle mode. The mode selector switch 91 is controlled from the console by a knob 276 on the cover. The console also includes a toggle handle 278 on the cover for manipulating the off-on power switch 29. The jacks 254, 256 are mounted on the cover 268.

To operate the epilator a plug 280 connected to a supply cord 282 for the epilator is plugged into a convenience electrical outlet. Then needle and/or tweezer are plugged into the corresponding jacks 254, 256. Next, power is turned on with the switch 29. The intensity of the desired radio frequency power is set with the variable resistors 246 and 248. The selector switch is set for either needle or tweezer operation. In case of needle operation, a suitable time is set with the variable resistor 180. This step is irrelevant for tweezer mode operation. The operation time for the tweezer is controlled by the duration of pressure on the foot pedal 138, whereas in the needle mode the foot pedal serves to initiate a suitable radio frequency power pulse when switched from the reset position.

The initiation of the timer circuit results in a DC pulse flowing according to FIG. 1 along the wire 154 and through the RF isolating coil 206 and the wire 208 to the RF oscillator 210. The oscillator feeds a pulse of RF energy via the lead 212 to the RF amplifier previously energized. In the circuit of FIG. 2 the output of the timer from the wire 426 is first amplified and then instantaneously switches on both the RF oscillator and the RF amplifier. The RF power output is fed through a power wire 240 to the blade 96 of the selector switch 91. Depending on the mode of the switch 91 the needle jack or the tweezer jack is fed with the RF power.

FIG. 7 shows a conventional application of the epilator with the subject sited near the epilator to reduce the length of the return path from the subject through the antenna to the chassis for the RF amplifier.

The following are typical values for the sundry components of FIGS. 1 and 2:

| COMPONENT Resistors | VALUE |
|---|---|
| 66 | 560 ohms |
| 76 | 560 ohms |
| 148 | 180K ohms |
| 160 | 560 ohms |
| 180 | 5 Meg ohms |
| 182 | 10K ohms |
| 192 | 10K ohms |
| 246 | 100 ohms |
| 248 | 100 ohms |

| COMPONENT Resistors | VALUE |
|---|---|
| 302 | 390 ohms |
| 304 | 390 ohms |
| 334 | 2K ohms |
| 364 | 100 ohms |
| 382 | 1K ohms |
| R2 | 10K ohms |
| R3 | 1K ohms |
| R4 | 1K ohms |
| R5 | 220 ohms |
| R6 | 100 ohms |
| R7 | 30 ohms |
| R8 | 120 ohms |
| R9 | 2.7K ohms |

| COMPONENT Capacitors | VALUE |
|---|---|
| 354 | 0.01μF |
| 394 | 10 pF |
| 430 | 0.1μF |
| C1 | 0.1μF |
| 152 | 0.47μF |
| C3 | 0.1μF |
| C4 | 0.01μF |
| C5 | 0.01μF |
| C6 | 150 pF |
| C7 | 0.01μF |
| C8 | 1000 pF |
| C9 | 0.01μF |
| C10 | 0.01μF |
| C11 | 47 pF |
| C12 | 50-150 pF |

| INDUCTANCES | VALUE |
|---|---|
| 104 | 1.5μH |
| 206 | 1.5μH |
| 238 | 1.5μH |
| 404 | 1.5μH |
| 416 | 1.5μH |
| 438 | 30μH |
| 440 | 30μH |
| 442 | 30μH |
| 444 | 30μH |

It thus will be seen that there are provided devices and methods which achieve the various objects of the invention and which are well adapted to meet the conditions of practical use.

As various possible embodiments might be made of the above invention, and as various changes might be made in the embodiments above set forth, it is to be understood that all matter herein described or shown in the accompanying drawings is to be interpreted as illustrative and not in a limiting sense.

Having thus described the invention, there is claimed as new and desired to be secured by Letters Patent:

1. An epilator comprising:
   (a) a DC power supply;
   (b) a controlled timer;
   (c) an RF power source coupled to said power supply and said timer and being energized from the power supply and switched by the timer, said RF power source having an output and a return;
   (d) means for connecting an individual hair of a person to the output of said RF power source;
   (e) an antenna connected to the return of said RF power source to provide a low impedance path for the radio frequency power from said person; and
   (f) means for starting and for resetting the timer.

2. An epilator according to claim 1 comprising a loading coil interposed between said antenna and said RF power source.

3. An epilator according to claim 1 wherein said antenna is a tuned antenna tuned for maximum efficiency.

4. An epilator according to claim 1 wherein said connecting means comprises:
   (a) switchable dual mode first and second outputs from said power source;
   (b) a first jack connected through a variable resistor to said first output;
   (c) a second jack connected through a variable resistor to said second output;
   (d) a needle for contacting the hair growth cells area and connected to a plug selectively engageable with the first jack; and
   (e) a tweezer for contacting a hair strand and connected to a plug selectively engageable with the second jack.

5. An epilator according to claim 1 wherein said DC power supply includes means to reduce and rectify line AC to DC.

6. An epilator according to claim 1 wherein the timer and the means for starting and resetting the timer comprise:
   (a) an integrated circuit;
   (b) an operator-controlled switch means for starting a timing cycle for said circuit; and
   (c) a network of resistors and capacitors connected to the switch means, the integrated circuit and the energizing DC power supply, the timer being operative to generate a DC pulse initiated by the switch means.

7. An epilator according to claim 6 wherein the RF power source comprises:
   (a) an RF oscillator powered by the DC pulse; and
   (b) an amplifier connected to the output of the oscillator.

8. An epilator according to claim 1 wherein the timer and the means for starting and resetting the timer comprise:
   (a) a timing circuit including the timer; and
   (b) a foot pedal connected to the timing circuit for energizing and resetting the timing circuit.

9. An epilator according to claim 1 wherein the connecting means and the starting and resetting means comprise:
   (a) a switch;
   (b) a first jack;
   (c) a first indicator light;
   (d) a first timing control circuit connected to said timer;
   (e) a second jack;
   (f) a second indicator light; and
   (g) a second timing control circuit connected to said timer,
said switch being connected to selectively energize either the first jack, the first indicator light and the first timing control circuit, or the second jack, the second indicator light and the second timing control circuit.

10. An epilator comprising:
    (a) a DC power supply;
    (b) a controlled timer;
    (c) a selector switch for selecting dual modes of operation;
    (d) means dually connecting the timer to the selector switch for enabling the timer to operate in two timing modes;
    (e) an RF power source connected to said power supply, said timer and said selector switch, and being energized from the power supply, switched by the timer and feeding to the selector switch;
    (f) a first variable impedance element connected to the selector switch for controlling the output of the RF power source;
    (g) a second variable impedance element connected to the selector switch for controlling the output of the RF power source;
    (h) a needle connected to the first variable element for contacting the hair growth cells area;
    (i) a tweezer connected to the second variable element for contacting a hair strand; and
    (j) an operator-controlled switch means connected to the timer for starting the same.

11. An epilator according to claim 10 wherein said RF power source includes a return, and further comprising a tuned antenna connected to the return of the RF power source.

12. An epilator comprising:
    (a) a DC power supply;
    (b) a manually variable electronic timer for operating in first and second modes, connected to and powered by the power supply and having an output;
    (c) an RF oscillator connected to and powered by the output of the timer and having an output;
    (d) an amplifier connected to the output of the RF oscillator and having an output;
    (e) means for selectively connecting to the output of the amplifier a needle connectable to a hair growth cells area and a tweezer connectable to a hair strand;
    (f) switch means connected to the timer for starting and resetting the timer; and
    (g) a selector switch connected to the amplifier output and the timer for selecting between needle and tweezer operation, and the mode in which said timer operates.

13. An epilator according to claim 12 wherein said switch means is a foot switch.

14. An epilator according to claim 13 further comprising a manually variable resistor connected to the timer for selecting a time for the output of the timer.

15. An epilator according to claim 14 wherein the selector switch includes means for connecting the variable resistor to the timer so as to set a finite time for the output of the timer when the selector switch is in the needle mode and wherein circuit means is included to cause the foot switch to initiate and terminate a time unlimited timer output when the selector switch is in the tweezer mode.

16. An epilator according to claim 14 further including means connected to the timer for defeating the operation of the variable resistor when the selector switch is set to tweezer operation, the output of the timer being turned on and off by the foot switch.

17. An epilator according to claim 12 further comprising:
 (a) a chassis, the RF oscillator and amplifier being mounted on the chassis, the amplifier having a return connected to the chassis;
 (b) an antenna; and
 (c) means connecting said antenna to the chassis so as to obtain efficient use of the RF frequency power and avoidance of RF broadcasting into the environment.

18. An epilator according to claim 17 wherein the amplifier is tuned to the frequency of the RF oscillator, the chassis being the voltage node of an electric dipole, and the hair strand connecting means and the antenna being the voltage lobes of the electric dipole.

19. A method for hair removal with radio frequency power generated by an epilator, said method comprising the steps of generating RF power, applying the generated RF power to a hair to be removed from a person, and employing an antenna to provide a low impedance RF circuit between the person being epilated and the epilator and to reduce emission of RF energy into the environment.

20. A method for hair removal with radio frequency power generated by an epilator, said method comprising the steps of generating the voltage lobe of an RF oscillating dipole at the end of a member, and connecting said member to a hair strand or hair growth cells area.

21. A method for hair removal with radio frequency power generated by an epilator, said method comprising the steps of employing a generator powered by a voltage supply line to generate the voltage node of an RF oscillating dipole at the chassis of the generator so as to keep RF power out of the voltage supply line, and coupling the generated RF power to a hair to be removed.

22. A method for hair removal with radio frequency power generated by an epilator, said method comprising the steps of employing a generator powered by a voltage supply line to generate RF power, permanently tuning said generator for maximum efficiency by constructing a balanced radio frequency oscillator dipole so as to eliminate the influence of the RF impedance of the voltage supply line on the generator operation, and coupling the generated RF power to a hair to be removed.

* * * * *